US012630854B2

(12) United States Patent
Geng

(10) Patent No.: US 12,630,854 B2
(45) Date of Patent: May 19, 2026

(54) METHOD FOR PREPARING GINSENOSIDE PREPARATION BY BIOLOGICAL ENGINEERING TECHNOLOGY

(71) Applicant: Mingzhiyuan (Hangzhou) Biological Technology Co., Ltd, Hangzhou (CN)

(72) Inventor: Shengli Geng, Hangzhou (CN)

( * ) Notice: Subject to any disclaimer, the term of this patent is extended or adjusted under 35 U.S.C. 154(b) by 392 days.

(21) Appl. No.: 18/268,927

(22) PCT Filed: Sep. 29, 2022

(86) PCT No.: PCT/CN2022/122383
§ 371 (c)(1),
(2) Date: Jun. 21, 2023

(87) PCT Pub. No.: WO2023/066002
PCT Pub. Date: Apr. 27, 2023

(65) Prior Publication Data
US 2024/0043901 A1 Feb. 8, 2024

(30) Foreign Application Priority Data

Oct. 19, 2021 (CN) .......................... 202111224254.8
Sep. 21, 2022 (CN) .......................... 202211150208.2

(51) Int. Cl.
| | |
|---|---|
| *C12P 33/20* | (2006.01) |
| *C12N 1/165* | (2026.01) |
| *C12N 1/205* | (2026.01) |
| *C12N 5/00* | (2006.01) |
| *C12R 1/225* | (2006.01) |
| *C12R 1/72* | (2006.01) |

(52) U.S. Cl.
CPC .............. *C12P 33/20* (2013.01); *C12N 1/165* (2021.05); *C12N 1/205* (2021.05); *C12N 5/0018* (2013.01); *C12N 2500/34* (2013.01); *C12N 2500/76* (2013.01); *C12R 2001/225* (2021.05); *C12R 2001/72* (2021.05)

(58) Field of Classification Search
CPC ........... C12P 33/20; C12P 19/56; C12P 33/00; C12N 1/165; C12N 1/205; C12N 5/0018; C12N 2500/34; C12N 2500/76; C12N 1/20; C12R 2001/225; C12R 2001/72; A23L 33/01; A23L 33/10
See application file for complete search history.

(56) References Cited

PUBLICATIONS

English Translation of CN 113881750 A, Jan. 2022, 7 pages of PDF (Year: 2022).*

* cited by examiner

*Primary Examiner — Kade Ariani*

(57) ABSTRACT

The invention discloses a method for preparing the ginsenoside preparation by biological engineering technology, wherein the ginsenoside preparation comprises at least one of the saponin-enriched preparation and the saponin-enriched syrup; the compound bio-enzyme preparation prepared by the combined bacteria preparation of yeast and lactic acid bacteria provided by the invention is rich in amino acid residues, amides, coenzymes and active groups such as lactic acid and linoleic acid; and the ginsenoside preparations containing ginsenosides can be prepared by adding monosaccharides or polysaccharides to the compound bio-enzyme preparations, providing new directions and ideas for obtaining ginsenosides and their products.

8 Claims, 3 Drawing Sheets

METHOD FOR PREPARING GINSENOSIDE PREPARATION BY BIOLOGICAL ENGINEERING TECHNOLOGY

1. TECHNICAL FIELD

The invention relates to the technical field of microbial applications, in particular to a method for preparing ginsenoside preparation by biological engineering technology.

2. BACKGROUND ART

Ginsenoside is a steroidal compound, also known as triterpene saponin. It is mainly found in medicinal herbs of the *ginseng* genus. Ginsenoside is considered as the active ingredient in *ginseng*, which has many effects such as anti-thrombotic, anti-fatigue, anti-aging, tumor control, immunity enhancement, and so on; wherein the ginsenoside Rg1 has the effects of quickly relieving fatigue, improving learning and memory, delaying aging, exciting central nervous system, inhibiting platelet aggregation and the like, and the ginsenoside Rf has the effects of weakening intestinal canal contraction caused by acetylcholine, with hemolytic activity. Ginsenosides are mostly found naturally in the roots, flower buds and stems of plants in the family of Araliaceae, such as *ginseng, panax notoginseng* and American *ginseng*. Currently, most of the saponins used for preparing ginsenoside preparations are extracted from these plants, but the content of ginsenosides in these plants is low and their extraction costs are high, which is difficult to meet the increasing demand for medicine.

3. SUMMARY OF THE INVENTION

To achieve the above objects and based on the above background, the invention provides a method for preparing ginsenoside preparation by biological engineering technology. The ginsenoside preparations containing ginsenosides were prepared by the compound bio-enzymes prepared by the combined bacteria preparation of yeast and lactic acid bacteria, and the prepared ginsenoside preparations can be used for the preparation of products with health care functions, which can provide new ideas and directions for the preparation of ginsenoside-related products.

The technical solutions provided by the invention are as follows:

A method for preparing ginsenoside preparation by biological engineering technology, wherein the ginsenoside preparation contains ginsenosides;

The ginsenoside preparation is prepared by the compound bio-enzyme preparation, and compound bio-enzyme preparation is prepared by the fermentation product of combined bacteria preparation of yeast and lactic acid bacteria;

The combined bacteria preparation of yeast and lactic acid bacteria comprises yeast and lactic acid bacteria;

The yeasts comprise *Candida ethanolica* B-JJ1, and the lactic acid bacteria comprise at least one of Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6.

The *Candida ethanolica* B-JJ1 with the deposit number: CCTCC NO: M2021136;

The *Lactobacillus buchneri* B-JR1 with the deposit number: CCTCC NO: M2021132;

The *Lactobacillus paracasei* B-JR2 with the deposit number: CCTCC NO: M2021133;

The *Lactobacillus zeae* B-JR4 with the deposit number: CCTCC NO: M2021135;

The *Lactobacillus plantarum* B-JR5 with the deposit number: CCTCC NO: M2021501;

The *Lactobacillus chiayiensis* B-JR6 with the deposit number: CCTCC NO: M2021502.

The method for preparing the ginsenoside preparation is as follows:

1) which can be prepared directly from a compound bio-enzyme preparation

Or 2) adding syrup to the compound bio-enzyme preparation in a ratio of 0-100% by volume thereof, stirring uniformly and then heating for preparation;

Or 3) adding solid sugar to the compound bio-enzyme preparation in the ratio of 0-100% by weight thereof, stirring uniformly and then heating for preparation.

Further, the ginsenoside preparation comprising at least one of the saponin-enriched preparations, the saponin-enriched syrup;

The preparation thereof comprises the following steps:

(1) Selecting the compound bio-enzyme preparation, and the compound bio-enzyme preparation being prepared from the fermentation product of the yeast and lactic acid bacteria combination;

(2) Adding the syrup to the compound bio-enzyme preparation in step (1) in a ratio of 0-100% by volume thereof and stirring uniformly;

(3) Heating the mixture of step (2);

(4) When the volume of the mixture of step (2) is evaporated to $\frac{1}{3}$-$\frac{2}{5}$ of the volume of the original mixture, then the saponin-enriched preparation is obtained;

(5) The saponin-enriched preparation of step (4) continues to heat until the volume after evaporation is equal to the amount added to the syrup of step (2), after cooling the material, then the saponin-enriched syrup can be obtained.

Further, the saponin-enriched preparations or saponin-enriched syrups can be applied to prepare solid ginsenoside preparations;

And the preparation method is as follows:

Saponin-enriched preparations or saponin-enriched syrups are foamed by shaking or passing air, and the foam is extracted after standing; then the foam is dehydrated at the temperature of 90-120° C. to obtain solid ginsenoside preparations.

Further, the syrup is a syrup made of monosaccharides.

Further, the syrup is fructose syrup.

Further, the syrup is a syrup prepared from at least one of glucose, sucrose, fructose, maltose and maltotriose but not limited to.

Further, the ginsenoside contained in the ginsenoside preparation comprises at least one of ginsenoside Rg1, ginsenoside Rf.

Further, the method for preparing the compound bio-enzyme preparation comprise the following steps:

(1) Selecting the yeast and lactic acid bacteria combination according to the claim 1 as the culture;

The combined bacteria preparation of yeast and lactic acid bacteria comprises yeast and lactic acid bacteria;

The yeasts comprise *Candida ethanolica* B-JJ1;

The lactic acid bacteria comprise at least one of Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6.

(2) Strain activation: moistening the mashed potato powder with sterile water at a weight ratio of 1:1, then mixing the strain with the moistened mashed potato powder at a weight ratio of 1:2 and carrying out aerobic activation in a sterile environment;

(3) Preparation and inoculation of the culture medium: the medium is prepared with mashed potato powder, wheat germ and glutinous rice as the main ingredients; the medium is steamed after adding water and stirring evenly, and the preparation of the medium has been completed when the temperature of the medium is cooled to below 45° C. in the aseptic conditions;

Mixing the prepared medium with the activated strain in step (2) in the ratio of 10:1 by weight.

(4) Adjusting the humidity of the culture medium after inoculation in step (3) to ensure that the medium remain water seeping when hold by hand and the whole medium is kept moist and breathable;

(5) Processing the aerobic fermentation of the medium in step (3) for over 48 hours until the medium uniformly appears white and milky white bacterial plaque to be visible with the naked eye, and then transferring the medium into the fermenter; solid fermentations can occupy one third of the fermenter; to close all channels of the fermenter to enable the medium fermentations into the tank to continue aerobic culture in the tank until the oxygen in the tank is depleted and enters the anaerobic fermentation state;

(6) When there is no pressure change in the fermenter, the solid-state fermentation enters into saturation fermentation, and there is a strong fermentation fragrance when opening the tank, with abundant mycelium covering the surface of the solid medium to be visible with the naked eye; taking the fermentation products for testing, and the total number of viable yeasts is 6.4× $10^4$-5.9×$10^5$ cfu/ml; the total number of viable lactic acid bacteria is 4×$10^8$-5.1×$10^9$ cfu/ml; and at this time the solid fermentation process has reached saturation point, and then enters the liquid fermentation stage;

(7) Adding the solid fermentation in the step (5) to sterile water and stirring thoroughly to dilute the metabolic substrate in the solid fermentation process; making sure that there is at least ⅕ space in the fermenter, and then carrying out aerobic activation and incubation for more than 72 hours until the surface of the liquid state fermentation is densely covered with white or milky white bacteria plaque, and to close all channels of the fermenter to enter anaerobic fermentation again when the aerobic fermentation has depleted the oxygen in the fermenter.

(8) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

Further, the method for preparing the compound bio-enzyme preparation further comprise the following steps:

(9) The material in step (8) was gradually warmed up to temperature between 78-88° C. for 2 hours, then cooled down; and extracting the supernatant of the ferment, to obtain the inactivated bio-enzyme preparation.

The application of the ginsenoside preparation according to claim 1 or 2 have applications in health function products.

Further, the health function products comprise the beverage products.

The invention also provides the application of purified powders prepared from ginsenoside preparations prepared using the above method in the pharmaceutical field.

Further, the health function products comprise the beverage products.

The compound bio-enzyme preparation prepared by the combined bacteria preparation of yeast and lactic acid bacteria provided by the invention is rich in amino acid residues, amides, coenzymes and active groups such as lactic acid and linoleic acid; and the ginsenoside preparations containing ginsenosides can be prepared by adding monosaccharides or polysaccharides to the compound bio-enzyme preparations, providing new directions and ideas for obtaining ginsenosides and their products.

4. BRIEF DESCRIPTION OF ACCOMPANY DRAWINGS

To make the technical solutions in the embodiments provided by the invention or in the prior art more comprehensible, a brief description of the drawings required in the description of the embodiments or prior art is given below, and it is obvious that drawings in the following description are only some of the embodiment provided by the invention and not the limitations of the scope of the disclosure. Other drawings can be obtained on the basis of these drawings without creative work by those of ordinary skill in the art.

FIG. 3 is a photograph showing the product of the ginsenoside preparation in solid powder prepared by the invention, wherein.

FIG. 3a shows the crude extracted solid ginsenoside preparation in the form of caramel-colored gelling paste;

FIG. 3b shows the primary purification of solid ginsenoside preparation;

FIG. 3c shows a third extraction foam preparation of a higher purity ginsenoside powder prepared after anhydrous ethanol extraction to reduce impurities;

FIG. 3d shows impurities such as amino acids precipitated during ethanol extraction.

FIG. 3e shows the residue of the filtrate;

FIG. 3f shows a high-purity ginsenoside preparation.

Figure 1:
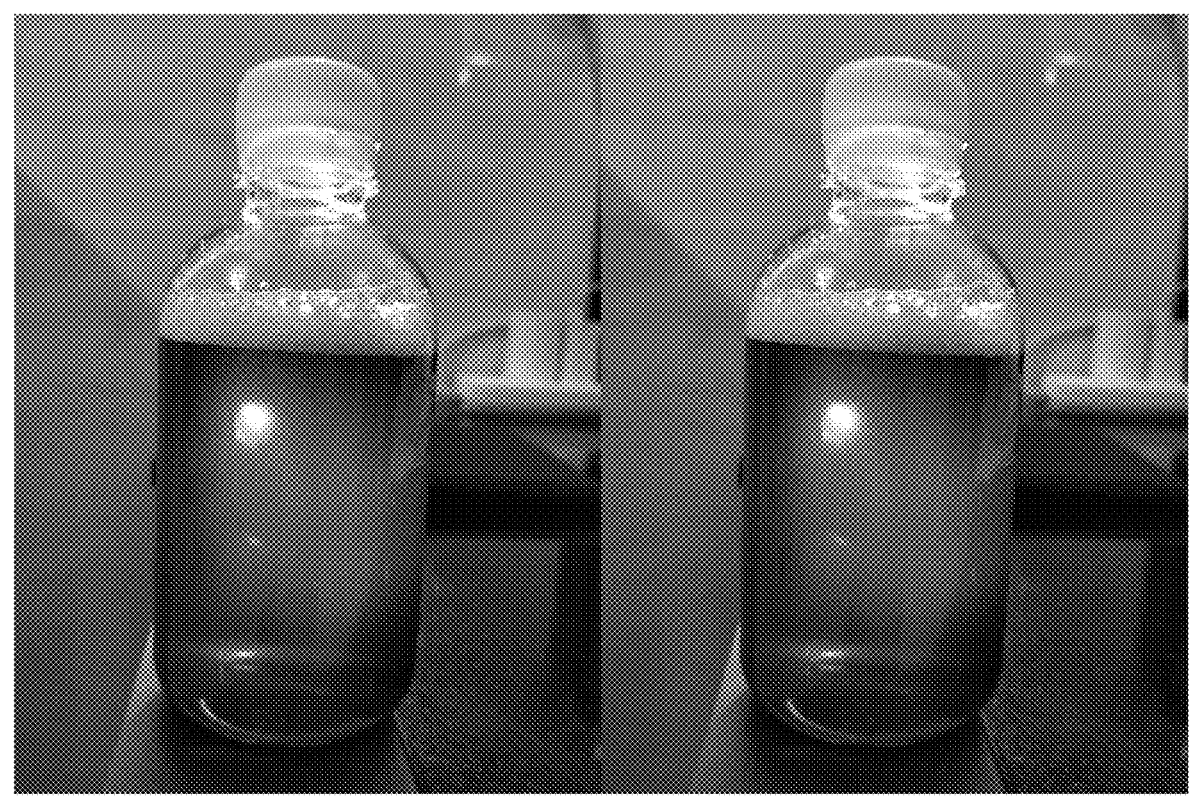
FIG. 1 is a photograph showing the ginsenoside preparation prepared by the invention.

The *Candida ethanolica* B-JJ1 provided by the invention with the deposit number: CCTCC NO: M2021136; the collection date is Jan. 21, 2021; the collection institution is China Center for Type Culture Collection (CCTCC); the deposit site is Wuhan University.

The *Lactobacillus buchneri* B-JR1 provided by the invention with the deposit number: CCTCC NO: M2021132; the collection date is Jan. 21, 2021; the collection institution is China Center for Type Culture Collection (CCTCC); the deposit site is Wuhan University.

The *Lactobacillus paracasei* B-JR2 provided by the invention with the deposit number: CCTCC NO: M2021133; the collection date is Jan. 21, 2021; the collection institution is China Center for Type Culture Collection (CCTCC); the deposit site is Wuhan University.

The *Lactobacillus zeae* B-JR4 provided by the invention with the deposit number: CCTCC NO: M2021135; the collection date is Jan. 21, 2021; the collection institution is China Center for Type Culture Collection (CCTCC); the deposit site is Wuhan University.

The *Lactobacillus plantarum* B-JR5 provided by the invention with the deposit number: CCTCC NO:

M2021501; the collection date is May 7, 2021; the collection institution is China Center for Type Culture Collection (CCTCC); the deposit site is Wuhan University.

The *Lactobacillus chiayiensis* B-JR6 provided by the invention with the deposit number: CCTCC NO: M2021502; the collection date is May 7, 2021; the collection institution is China Center for Type Culture Collection (CCTCC); the deposit site is Wuhan University.

5. SPECIFIC EMBODIMENT OF THE INVENTION

To make the purpose, technical solutions and advantages of the embodiments provided by the invention more comprehensible, a further description of the invention is given below in combination with the attached drawings and embodiments, and the embodiments are exemplary and not the limitations of the scope of the disclosure. It is clear that the embodiments in the following description are a part of the embodiments provided by the invention instead of all of them. Based on the embodiments in the invention, all other embodiments obtained by those of ordinary skill in the art without making creative effort shall fall within the scope of protection of the invention.

A further description of the invention is given below in combination with the attached drawings and embodiments.

Embodiment 1

The cultivation of *Candida ethanolica* B-JJ1, Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6 in the yeast and lactic acid bacteria combination used in the preparation of the compound bio-enzyme preparation provided by the invention can be referred to the invention patent with application number 202111198135X, and one of the cultivation methods comprises the following steps:

(1) Inoculum extraction: taking the pit mud fermentation from the Chinese liquor brewing mud pit form the different orientation, and the different directions mentioned refer to the east, south, west and north, the pit walls and the bottom of the pit;

Adding sterile water with the temperature of 35-38° C. to the pit mud fermentation in accordance with the weight ratio of 2:1, and letting stand for use after mixing sufficiently;

The brewing pit in this embodiment is a traditional brewing pit of Chinese liquor in the Yaowan ancient town in northern Jiangsu Province.

(2) Culture medium preparation: taking 4 parts of sorghum rice, 3 parts of mashed potato powder, 1 part of wheat germ, 1 part of buckwheat and 1 part of glutinous rice as the main ingredients for preparation; taking raw materials in accordance with the weight ratio of 1:1 and adding water and stirring sufficiently; and after steam distillation for 40 minutes until the granular swelling, the culture medium can be placed in a sterile container for heat dissipation; and cooling the temperature of medium to below 45° C. for use;

(3) Strain inoculation: the pit mud fermentation in the step (1) and the prepared medium in the step (2) are mixed evenly according to the weight ratio of 1:2, and then placed in an aseptic conditions with the temperature above 26° C. for constant temperature aerobic cultivation for over 45 hours and it is necessary to pay attention to the medium changes during this process;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags according to 1-5 kg respectively and the medium will continue to ferment at a constant temperature of 37° C. after being packed in separate bags.

In this step, due to the previous culture with a large number of aerobic colonies, there will be the output of gas after sealing the bag, therefore, it is necessary to pay attention to the appropriate time to release the gas and reduce the pressure.

(5) Obtain facultative anaerobes yeast and lactic acid bacteria combination: after depleting the residual oxygen in the bag, the medium in the bag appears agglomeration in vacuum with white, creamy white bacterial plaque and covered with bacterial film. When covered by the bacterial film, a variety of aerobic bacteria of *Aspergillus* and *Mucor* species will enter into apoptosis, the main survival with slow proliferation is facultative anaerobe yeast and lactic acid bacteria combination.

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation; the aerobic bacteria have almost no survival conditions at this time (there may exist a very few fungal spores but they will be completely eliminated due to the suppression of community dominance and subsequent processes); at the same time, the facultative anaerobe bacteria are gradually entering a dormant state and waiting for recovery;

(7) Sampling and testing to identify the obtained symbiotic colonies: testing the activity of the combined bacteria in the step (6), and when the average value of viable yeast is $6.4 \times 10^4$ cfu/ml or more; the average value of viable lactic acid bacteria is $4 \times 10^8$ cfu/ml or more, the first generation of yeast and lactic acid bacteria combination is obtained.

In this embodiment, the maximum value of viable yeast is $3.1 \times 10^5$ cfu/ml and the maximum value of viable lactic acid bacteria is $1.2 \times 10^9$ cfu/ml.

(8) Combined bacteria domestication: due to the acquisition of the combined colonies, out of the complementary of the large communities of *Aspergillus* and *Mucor*, forming symbiotic adaptations between new small communities, adaptations to the medium and adaptations to changes in the survival environment such as the conversion of aerobic and anaerobic environments, therefore it is necessary to domesticate the combined bacteria. Mixing the medium in the step (2) with the first generation of yeast and lactic acid bacteria combination in the step (7) according to the weight ratio of 1:1, and spraying sterile water until moistened to wet and scattered, with water dripping out when hold by hand; then placing it in sterile condition with the temperature above 26° C. for more than 48 hours of aerobic activation, until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation for 20-30 days until the colony yeast and lactic acid bacteria combination grows vigorously;

(9) Packaging of the combined bacteria: the domesticated yeast and lactic acid bacteria combination in the step (8) are vacuum packed according to 5-10 kg/bag, isolation of air to eliminate aerobic bacterial infection and thoroughly eliminate the possible residual by the first generation of strains of *Aspergillus, Mucor* and other fungal spores, thus allowing easy industrial transport and application.

This embodiment tested the yeast and lactic acid bacteria combination after packaging in step (9), the average value of viable yeast is more than $6.4 \times 10^4$ cfu/ml, the average value of viable lactic acid bacteria is more than $4 \times 10^8$ cfu/ml, the value of the mould in harmful bacteria is <10 cfu/ml; *Escherichia coli* is <30 cfu/ml; *Salmonella* ND; *Shigella* ND; *Staphylococcus aureus* ND (ND means not detected).

The invention can be purified and separated according to the actual needs, and then mixed and formulated into a combination of bacteria with different properties, for example, yeast and lactic acid bacteria combination of the invention can include *Candida ethanolica* B-JJ1, Lentilactobacillus *buchneri* B-JR1, *Lactobacillus lactis* B-JR6; or *Candida ethanolica* B-JJ1, Lentilactobacillus *buchneri* B-JR1, *Lactobacillus paracasei* B-JR2, *Lactobacillus chiayiensis* B-JR6; or *Candida ethanolica* B-JJ1, and the lactic acid bacteria comprise Lentilactobacillus *buchneri* B-JR1, *Lactobacillus paracasei* B-JR2, *Lactobacillus zeae* B-JR4, *Lactobacillus chiayiensis* B-JR6.

Embodiment 2

The method for preparing the compound bio-enzyme preparation comprises the following steps:

(1) selecting the yeast and lactic acid bacteria combination according to the claim 1 as the culture;

The combined bacteria preparation of yeast and lactic acid bacteria comprises yeast and lactic acid bacteria;

The yeasts comprise *Candida ethanolica* B-JJ1;

The lactic acid bacteria comprise at least one of Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6.

(2) Strain activation: moistening the mashed potato powder with sterile water at a weight ratio of 1:1, then mixing the strain with the moistened mashed potato powder at a weight ratio of 1:2 and carrying out aerobic activation in a sterile environment;

(3) Preparation and inoculation of the culture medium: the medium is prepared with mashed potato powder, wheat germ and glutinous rice as the main ingredients; the medium is steamed after adding water and stirring evenly, and the preparation of the medium has been completed when the temperature of the medium is cooled to below 45° C. in the aseptic conditions;

Mixing the prepared medium with the activated strain in step (2) in the ratio of 10:1 by weight.

The preparation process of the medium comprises the following steps:

After washing sorghum rice, buckwheat, glutinous rice in the ratio of 50:10:20, and then mixed with the 10% wheat germ, 10% mashed potatoes powder; the medium is steamed after mixing well with water in the ratio of 1:1, and the preparation of the medium has been completed when the temperature of the medium is cooled to below 45° C. in the aseptic conditions;

(4) Adjusting the humidity of the culture medium after inoculation in step (3) to ensure that the medium remain water seeping when hold by hand and the whole medium is kept moist and breathable;

(5) Processing the aerobic fermentation of the medium in step (3) for over 48 hours until the medium uniformly appears white and milky white bacterial plaque to be visible with the naked eye, and then transferring the medium into the fermenter; solid fermentations can occupy one third of the fermenter; to close all channels of the fermenter to enable the medium fermentations into the tank to continue aerobic culture in the tank until the oxygen in the tank is depleted and enters the anaerobic fermentation state;

(6) When there is no pressure change in the fermenter, the solid-state fermentation enters into saturation fermentation, and there is a strong fermentation fragrance when opening the tank, with abundant mycelium covering the surface of the solid medium to be visible with the naked eye; taking the fermentation products for testing, and the total number of viable yeasts is $6.4 \times 10^4$-$5.9 \times 10^5$ cfu/ml; the total number of viable lactic acid bacteria is $4 \times 10^8$-$5.1 \times 10^9$ cfu/ml; and at this time the solid fermentation process has reached saturation point, and then enters the liquid fermentation stage;

(7) Adding the solid fermentation in the step (5) to sterile water and stirring thoroughly to dilute the metabolic substrate in the solid fermentation process; making sure that there is at least ⅓ space in the fermenter, and then carrying out aerobic activation and incubation for more than 72 hours until the surface of the liquid state fermentation is densely covered with white or milky white bacteria plaque, and to close all channels of the fermenter to enter anaerobic fermentation again when the aerobic fermentation has depleted the oxygen in the fermenter.

(8) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

(9) The material in step (8) was gradually warmed up to temperature between 78-88° C. for 2 hours, then cooled down; and extracting the supernatant of the ferment, to obtain the inactivated bio-enzyme preparation.

The step is the process of inactivation of the bio-enzyme preparation, and the specific operation is as follows:

The material of step (8) will be gradually warmed up to 78-88° C. (maintain 55° C. for one hour after warming up), and then slowly warmed up to between 78-88° C., after a total of two hours, cooling to room temperature by passing cold water into the tank interlayer; and extracting the supernatant of the ferment, to obtain the inactivated bio-enzyme preparation.

Testing the total saponin content of the bio-enzyme preparation prepared in step (9) in this embodiment, and the test results of the total saponin content in the bio-enzyme preparation used in the invention is 1260 mg/L (Report No.: 2021SP00507R01).

This test was done by the Guangdong Microbiological Analysis and Testing Center according to the "Health Food Inspection and Evaluation Technical Specification" (2003 edition) in the health food efficacy components and health indicators test specification Part II (Part XXIII, the determination of total saponins in health food) P306-307, the following test on the total saponin content is adopted the same method if not further mentioned.

Embodiment 3

A method for preparing ginsenoside preparation by biological engineering technology, wherein the ginsenoside preparation is a saponin-enriched preparation.
The preparation thereof comprises the steps of
(1) Selecting the compound bio-enzyme preparation prepared in embodiment 2;
(2) Heating the compound bio-enzyme preparation in step (1) to 160° C. until its volume after evaporation to ⅓ of the volume of the raw material, to obtain the saponin-enriched preparation.
Testing the total saponin content of the saponin-enriched preparation prepared in step (2) in this embodiment, and the test results of the total saponin content is 3700 mg/L (Report No.: 2021SP01348R01).

Embodiment 4

A method for preparing ginsenoside preparation by biological engineering technology, wherein the ginsenoside preparation is a saponin-enriched preparation.
The preparation thereof comprises the steps of
(1) Selecting the compound bio-enzyme preparation prepared in embodiment 2;
(2) Adding fructose syrup with type F55 to the bio-enzyme preparation in step (1) at a ratio of 4% by volume and mixing well.
(3) Heating the compound bio-enzyme preparation in step (1) to above 160° C.
(4) To obtain the saponin-enriched preparation until its volume after evaporation to ⅓ of the volume of the raw material;
Testing the total saponin content of the saponin-enriched preparation prepared in step (4) in this embodiment, and the test results of the total saponin content is 7600 mg/L (Report No.: 2021 SP01348R02).
This embodiment combined with the comparison with embodiment 3, the total saponin content of the saponin-enriched preparation prepared in this embodiment is more than two times the total saponin of the saponin-enriched preparation prepared in embodiment 3, it can be reasonably presumed that the added fructose syrup reacts with the bio-enzyme preparation, and there is a new saponin generated on the basis of the original total saponin.
And this embodiment tried to add glucose syrup to the prepared bio-enzyme preparation in the bio-enzyme preparation step (8) of embodiment 2, and then follow step (9) for heat inactivation; and the total saponin of the inactivated bio-enzyme preparation after the addition of glucose syrup was detected, and its total saponin content was 1580 mg/L, slightly higher than the total saponin content of the directly inactivated bio-enzyme preparation in embodiment 1, it is assumed that the total saponin concentration may have changed a little due to the reaction between the glucose syrup and the bio-enzyme preparation during inactivation.

10

Embodiment 5

A method for preparing ginsenoside preparation by biological engineering technology, wherein the ginsenoside preparation is a saponin-enriched preparation.
The preparation thereof comprises the steps of
(1) Selecting the compound bio-enzyme preparation prepared in embodiment 2;
(2) Adding fructose syrup with type F55 to the bio-enzyme preparation in step (1) at a ratio of 15% by volume and mixing well.
(3) Heating the compound bio-enzyme preparation in step (1) to above 160° C.
(4) To obtain the saponin-enriched preparation until its volume after evaporation to ⅖ of the volume of the raw material;
Testing the total saponin content of the saponin-enriched preparation prepared in step (4) in this embodiment, and the test results of the total saponin content is 18000 mg/L (Report No.: 2021SP03577R04). From this data it can be further reasonably inferred that the increase in the total saponin content obtained in step (4) was generated by the reaction of the syrup with the bio-enzyme preparation rather than simply enriched by heating.

Embodiment 6

A method for preparing ginsenoside preparation by biological engineering technology, wherein the ginsenoside preparation is a saponin-enriched preparation.
The preparation thereof comprises the steps of
(1) Selecting the compound bio-enzyme preparation prepared in embodiment 2;
(2) Adding fructose syrup to the bio-enzyme preparation in step (1) at a ratio of 100% by volume and mixing well.
(3) Heating the compound bio-enzyme preparation in step (1) to above 160° C.
(4) When the volume after evaporation in the mixture of step (2) is equal to the volume of the added fructose syrup, a saponin-enriched syrup is obtained.
Testing the total saponin content of the saponin-enriched preparation prepared in step (4) in this embodiment, and the test results of the total saponin content is 16000 mg/L (Report No.: 2021 SP06170R02).
The invention uses a method of preparing ginsenosides by co-mingling and heating of bio-enzyme preparations with syrup, with the presumed reaction principle as follows.
It is mainly available in bio-enzyme preparations with abundant free active groups (amino acid residues, amides, coenzymes and active groups such as lactic acid, linoleic acid) through a series of enzymatic, acidolysis, hydrolysis, heating catalyzed dehydration condensation, acyl modification, etc., and then use the polyhydroxy aldehyde, polyhydroxy ketone characteristics of monosaccharides, and has the properties of polyhydroxylation reaction, oxidative esterification reaction, acetal reaction, aldehyde group, carbonyl reaction; after multiple reactions such as heating and catalysis, saponins mainly based on saponin Rf,Rg1 were generated, and because the active ingredients in the bio-enzyme preparation are more complex, the specific mechanism concerning the preparation of saponins from bio-enzyme preparation plus monosaccharide sources needs to be experimentally verified.

Embodiment 7

A method for preparing ginsenoside preparation by biological engineering technology, wherein the ginsenoside preparation is a saponin-enriched preparation.

The preparation thereof comprises the steps of (1) Selecting the compound bio-enzyme preparation prepared in embodiment 2;

(2) Adding disaccharide—Icing sugar crystals to the bio-enzyme preparation in step (1) at a ratio of 25% by volume and mixing well.

(3) Heating the compound bio-enzyme preparation in step (1) to above 100° C. and processing the hydrolysis of icing sugar resulting from the conversion of disaccharides to monosaccharides.

(4) Heating up the mixture of step (3) to above 160° C. to continue heating up and condensing.

(5) To obtain the saponin-enriched preparation until its volume after evaporation to ⅔ of the volume of the raw material;

Testing the total saponin content of the saponin-enriched preparation prepared in step (5) in this embodiment, and the test results of the total saponin content is 66000 mg/L (Report No.: 2021SP07432R01). This embodiment illustrates that polysaccharide, such as icing sugar, granulated sugar, brown sugar, and other disaccharides can also be used to generate saponins by reacting with bio-enzyme preparations, with the presumption that polysaccharides will first generate monosaccharides by hydrolysis upon heating, such as disaccharide $C_{12}H_{22}O_{11}$ heated and hydrolyzed to monosaccharide $C_6H_{12}O_6$, and then the monosaccharides will then participate in the reaction to generate saponins.

Photographs of the ginsenoside preparations prepared in Embodiments 3 to 7 are shown in the accompanying drawings, which may be reddish brown or brown in color.

Embodiment 8

The invention adopts the saponin-enriched preparation prepared in embodiment 7 to prepare a solid ginsenoside preparation.

Figure 2:
FIG. 2 is a photograph showing the process of preparing a ginsenoside preparation in solid powder by the invention.

The preparation method is as follows:

The saponin-enriched preparation prepared in embodiment 7 was cooled to below 40° C., foamed by shaking or passing air, and extracted foam after standing; repeatedly operated to extract until no foam was produced; then the extracted foam was dehydrated at 90-120° C. to prepare a caramel-colored gelling paste of solid ginsenoside preparations, which is the crude extraction of solid ginsenoside preparations. FIG. 2 is a photograph showing the preparation process of saponin-enriched preparations, and a photograph of the crude extracted solid ginsenoside preparation product is shown in FIG. 3a.

Figure 3:
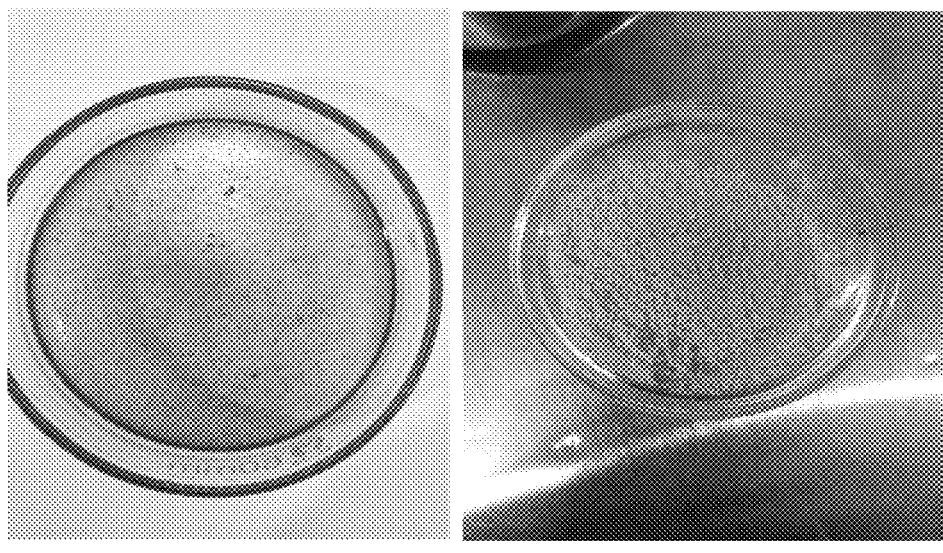
Figure 3:
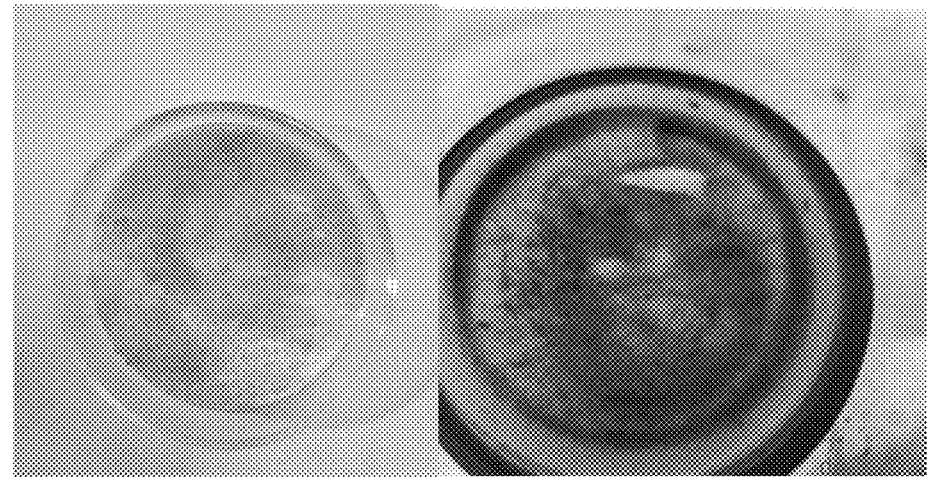
Figure 3:
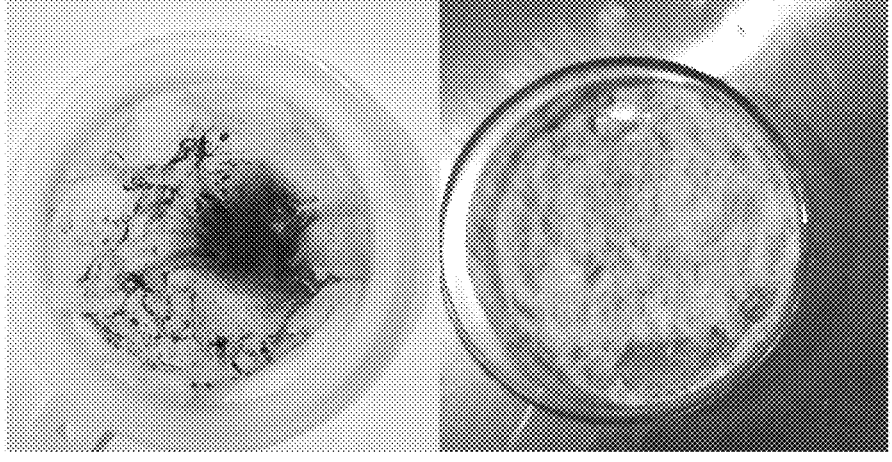

In specific implementation, the above crude extraction of solid ginsenoside preparations with distilled water for water dilution of more than ten times; repeatedly operated the following steps: foamed by shaking or passing air, and extracted foam after standing; repeatedly operated to extract until no foam was produced; then the extracted foam was dehydrated at 90-120° C. to prepare a caramel-colored solid ginsenoside preparations, which is the primary purified solid ginsenoside preparations; as the product photos referring to FIG. 3b, this operation was performed to wash out other water-soluble impurities of the preparation and to further purify the saponin preparation.

Further, the above primary purification of solid ginsenoside preparations are processed by adding anhydrous ethanol ten times for dissolution, precipitation and separation of amino acids and other impurities, after standing clarification, with 400 mesh filter paper or filter cloth, to filter out the ethanol solution, after evaporation of ethanol to obtain the Rg1, Rf mixed preparation powder shown in FIG. 3c, FIG. 3d for the precipitate residue, FIG. 3e for the filtered residue.

The saturated aqueous solution of n-butanol was taken to fully dissolve the mixed preparation powder of Rg1 and Rf, extract ginsenosides, discard the aqueous solution, recover n-butanol under reduced pressure, to prepare a high-purity ginsenoside preparation, referring to the FIG. 3f.

Embodiment 9

To prepare beverages using embodiments 3 to embodiment 7, during the preparation of the beverage, the raw materials conventionally used in the preparation of beverages can be added, for example, it can be diluted with water, or also added juice for flavoring; or just packaged directly.

The beverage prepared in embodiment 4 was tested by the National Center for Quality Supervision and Inspection of Food Machinery using the standard control method (Report No.: 2129053), and the content of ginsenoside Rf was detected as 333.6 mg/L, and the content of ginsenoside Rg1 as 1318 mg/L.

Prepared beverages produced by processing the ginsenoside preparations prepared by the invention can be stored for a long time (not less than two years) without the addition of preservatives, and the compound bio-enzyme preparation used in the invention can be used as a preservative (referring to the invention Patent No. 202111198135X, which will not be repeated here), so the beverage with health function prepared by the ginsenoside preparation of the invention is safer and healthier.

In specific implementation, the ginsenoside preparation prepared by the invention can be purified according to the demand for ginsenoside, so that it can provide new ideas and directions for the pharmaceutical application of ginsenoside and its ginsenoside products.

The invention and the embodiments thereof are described hereinabove, and this description is not restrictive. What is shown in the drawing is only the principles and one of the preferred embodiments of the invention, and the actual structure is not limited thereto. In summary, any equivalent structures or equivalent process transformations made by using the specifications and the attaching drawings of the invention, or direct or indirect applications to other related technical fields, shall all fall within the protection scope of the invention.

What is claimed is:

1. A method for preparing ginsenoside preparation by biological engineering technology, wherein the ginsenoside preparation contains ginsenosides;

the ginsenoside preparation is prepared by the compound bio-enzyme preparation, and compound bio-enzyme preparation is prepared by the fermentation product of combined bacteria preparation of yeast and lactic acid bacteria;

the combined bacteria preparation of yeast and lactic acid bacteria comprises yeast and lactic acid bacteria;

the yeasts comprise *Candida ethanolica* B-JJ1, and the lactic acid bacteria comprise at least one of Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6;

the *Candida ethanolica* B-JJ1 with the deposit number: CCTCC NO: M2021136;

the *Lactobacillus buchneri* B-JR1 with the deposit number: CCTCC NO: M2021132;

the *Lactobacillus paracasei* B-JR2 with the deposit number: CCTCC NO: M2021133;

the *Lactobacillus zeae* B-JR4 with the deposit number: CCTCC NO: M2021135;

the *Lactobacillus plantarum* B-JR5 with the deposit number: CCTCC NO: M2021501;

the *Lactobacillus chiayiensis* B-JR6 with the deposit number: CCTCC NO: M2021502;

the method for preparing the ginsenoside preparation is as follows:

1) adding a syrup to the compound bio-enzyme preparation in a ratio of 1-100% by volume thereof, stirring uniformly and then heating for preparation;

or 2) adding solid sugar to the compound bio-enzyme preparation in the ratio of 1-100% by weight thereof, stirring uniformly and then heating for preparation.

2. The method for preparing ginsenoside preparation by biological engineering technology according to the claim 1, wherein the ginsenoside preparation comprising at least one of the saponin-enriched preparations, the saponin-enriched syrup;

the preparation thereof comprises the following steps:

(1) selecting the compound bio-enzyme preparation, and the compound bio-enzyme preparation being prepared from the fermentation product of the yeast and lactic acid bacteria combination;

(2) adding the syrup to the compound bio-enzyme preparation in step (1) in a ratio of 0-100% by volume thereof and stirring uniformly;

(3) heating the mixture of step (2);

(4) when the volume of the mixture of step (2) is evaporated to ⅓-⅖ of the volume of the original mixture, then the saponin-enriched preparation is obtained;

(5) the saponin-enriched preparation of step (4) continue to heat until the volume after evaporation is equal to the amount added to the syrup of step (2), after cooling the material, then the saponin-enriched syrup is obtained.

3. The method for preparing ginsenoside preparation by biological engineering technology according to the claim 2, wherein the saponin-enriched preparations or saponin-enriched syrups are applied to prepare solid ginsenoside preparations.

4. The method for preparing ginsenoside preparation by biological engineering technology according to claim 1, wherein the syrup is the syrup made of monosaccharaides.

5. The method for preparing ginsenoside preparation by biological engineering technology according to the claim 4, wherein the syrup is fructose syrup.

6. The method for preparing ginsenoside preparation by biological engineering technology according to claim 1, wherein the syrup is a syrup prepared from at least one of glucose, sucrose, fructose, maltose and maltotriose.

7. The method for preparing the compound bio-enzyme preparation used in the method for preparing ginsenoside preparations by biological engineering technology according to claim 1, wherein the method for preparing the compound bio-enzyme preparation comprise the following steps:

(1) selecting the yeast and lactic acid bacteria combination according to the claim 1 as the culture;

the combined bacteria preparation of yeast and lactic acid bacteria comprises yeast and lactic acid bacteria;

the yeasts comprise *Candida ethanolica* B-JJ1;

the lactic acid bacteria comprise at least one of Lentilactobacillus *buchneri* B-JR1, *Lactobacillus paracasei* B-JR2, *Lactobacillus zeae* B-JR4, *Lactobacillus plantarum* B-JR5 and *Lactobacillus chiayiensis* B-JR6;

(2) strain activation: moistening the mashed potato powder with sterile water at a weight ratio of 1:1, then mixing the strain with the moistened mashed potato powder at a weight ratio of 1:2 and carrying out aerobic activation in a sterile environment;

(3) preparation and inoculation of the culture medium: the medium is prepared with mashed potato powder, wheat germ and glutinous rice as the main ingredients; the medium is steamed after adding water and stirring evenly, and the preparation of the medium has been completed when the temperature of the medium is cooled to below 45° C. in the aseptic conditions;

mixing the prepared medium with the activated strain in step (2) in the ratio of 10:1 by weight;

(4) adjusting the humidity of the culture medium after inoculation in step (3) to ensure that the medium remain water seeping when hold by hand and the whole medium is kept moist and breathable;

(5) processing the aerobic fermentation of the medium in step (3) for over 48 hours until the medium uniformly appears white and milky white bacterial plaque to be visible with the naked eye, and then transferring the medium into the fermenter; solid fermentations can occupy one third of the fermenter; to close all channels of the fermenter to enable the medium fermentations into the tank to continue aerobic culture in the tank until the oxygen in the tank is depleted and enters the anaerobic fermentation state;

(6) when there is no pressure change in the fermenter, the solid-state fermentation enters into saturation fermentation, and there is a strong fermentation fragrance when opening the tank, with abundant mycelium covering the surface of the solid medium to be visible with the naked eye; taking the fermentation products for testing, and the total number of viable yeasts is $6.4\times10^4$-$5.9\times10^5$ cfu/ml; the total number of viable lactic acid bacteria is $4\times10^8$-$5.1\times10^9$ cfu/ml; and at this time the solid fermentation process has reached saturation point, and then enters the liquid fermentation stage;

(7) adding the solid fermentation in the step (5) to sterile water and stirring thoroughly to dilute the metabolic substrate in the solid fermentation process; making sure that there is at least ⅓ space in the fermenter, and then carrying out aerobic activation and incubation for more than 72 hours until the surface of the liquid state fermentation is densely covered with white or milky white bacteria plaque, and to close all channels of the fermenter to enter anaerobic fermentation again when the aerobic fermentation has depleted the oxygen in the fermenter;

(8) when the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

8. The method for preparing the compound bio-enzyme preparation used in the method for preparing ginsenoside preparations by biological engineering technology according to claim 7, wherein the method for preparing the compound bio-enzyme preparation further comprise the following steps:

(9) the material in step (8) was gradually warmed up to temperature between 78-88° C. for 2 hours, then cooled down; and extracting the supernatant of the ferment, to obtain the inactivated bio-enzyme preparation.

\* \* \* \* \*